(12) United States Patent
Hwang et al.

(10) Patent No.: US 9,213,086 B2
(45) Date of Patent: Dec. 15, 2015

(54) COMPUTED VOLUME SONOGRAPHY

(75) Inventors: Juin-Jet Hwang, Mercer Island, WA (US); Clinton T. Siedenburg, Everett, WA (US); Ramachandra Pailoor, Woodinville, WA (US); Mitchell Kaplan, Lake Forest Park, WA (US); Garet G. Nenninger, Seattle, WA (US)

(73) Assignee: FUJIFILM SonoSite, inc., Bothell, WA (US)

(*) Notice: Subject to any disclaimer, the term of this patent is extended or adjusted under 35 U.S.C. 154(b) by 1588 days.

(21) Appl. No.: 11/768,678

(22) Filed: Jun. 26, 2007

(65) Prior Publication Data
US 2008/0287789 A1    Nov. 20, 2008

Related U.S. Application Data

(60) Provisional application No. 60/917,792, filed on May 14, 2007.

(51) Int. Cl.
*G01S 7/52*        (2006.01)
*G01S 15/89*       (2006.01)

(52) U.S. Cl.
CPC ......... *G01S 7/52074* (2013.01); *G01S 15/8993* (2013.01)

(58) Field of Classification Search
CPC ............................. A61B 8/5207; A61B 8/145
USPC .................................. 600/407, 437, 447, 463
See application file for complete search history.

(56) References Cited

U.S. PATENT DOCUMENTS

| 4,497,210 | A | * | 2/1985 | Uchida et al. ................... 73/602 |
| 4,817,434 | A |   | 4/1989 | Anderson |
| 5,795,297 | A |   | 8/1998 | Daigle |
| 5,906,580 | A | * | 5/1999 | Kline-Schoder et al. ..... 600/459 |
| 6,023,660 | A |   | 2/2000 | Dory et al. |
| 6,028,547 | A |   | 2/2000 | Dory et al. |
| 6,436,039 | B1 |  | 8/2002 | Lannutti et al. |
| 6,511,426 | B1 |  | 1/2003 | Hossack et al. |

(Continued)

FOREIGN PATENT DOCUMENTS

WO    WO-2006/113445    10/2006

OTHER PUBLICATIONS

Gorfu, Y., et al., "Parallel Computation for Rapid Reconstruction of Volumetric Ultrasonic Images," IEEE Proceedings on Ultrasonics Symposium, Oct. 20, 1992, pp. 1129-1132.

(Continued)

*Primary Examiner* — Rochelle Turchen
(74) *Attorney, Agent, or Firm* — Perkins Coie LLP (57) ABSTRACT

A system performs ultrasound parameter estimation at specific advantageous sets of points in a two- or three-dimensional field of view within re-configurable, massively parallel, programmable architectures. A power efficient system is used for processing the data, thereby increasing the ability of the system for mobile ultrasound applications. Various architectural aspects provide the ability to simultaneously accept a large number of channels of data characterized by a continuous, simultaneous flow at high sample rates. The input data is routed at high rates to a distributed and large number of processing elements, memory, and connections for simultaneous parameter estimation at multiple points in the field of view, thereby enabling data streaming through the architecture.

54 Claims, 7 Drawing Sheets

(56) References Cited

U.S. PATENT DOCUMENTS

| | | | |
|---|---|---|---|
| 6,595,921 B1* | 7/2003 | Urbano et al. | 600/437 |
| 6,685,645 B1 | 2/2004 | McLaughlin et al. | |
| 7,970,279 B2* | 6/2011 | Dress | 398/66 |
| 2003/0216645 A1* | 11/2003 | Yao et al. | 600/437 |
| 2004/0015079 A1* | 1/2004 | Berger et al. | 600/437 |
| 2004/0254439 A1* | 12/2004 | Fowkes et al. | 600/407 |
| 2005/0262031 A1* | 11/2005 | Saidi et al. | 706/21 |
| 2006/0229513 A1* | 10/2006 | Wakai | 600/407 |

OTHER PUBLICATIONS

Diefendorff, K., et al., "Altivec Extension to PowerPC Accelerates Media Processing," IEEE Micro, Mar. 1, 2000, pp. 85-95, vol. 20, No. 2.

Extended European Search Report for European Patent Application No. EP 08251653 mailed on Feb. 1, 2012, 11 Pages.

State Intellectual Property Office of the People's Republic of China, Third Office Action, counterpart CN Patent Application 200810096180.2, mailed Dec. 5, 2012, 18 pages (includes English translation).

State Intellectual Property Office of the People's Republic of China, First Office Action, counterpart CN Patent Application 200810096180.2, mailed Jun. 3, 2011, 9 pages (includes English translation).

Second Office Action for Chinese Patent Application No. CN 200810096180.2, Apr. 28, 2012, 5 pages.

\* cited by examiner

FIG. 7D ing. The filters can also be used to match element characteristics to overcome limitations due to variations in the manufacturing processes of the transducer or element, interconnect and channel imperfections, or transducer aging. By correcting for channel imperfections and variations, the system is more robust to noise than conventional systems.

COMPUTED VOLUME SONOGRAPHY

CROSS-REFERENCE TO RELATED APPLICATIONS

This Application is a Non-Provisional of U.S. Provisional (35 USC 119(e)) Application No. 60/917,792 filed May 14, 2007.

TECHNICAL FIELD OF THE INVENTION

In the field of sonography, ultrasound images are produced by an ultrasound imaging system (scanner) that includes a transducer to ensonify (transmit ultrasound energy into) an anatomical region of interest and to receive the energy response of the tissue. Typically, the system controls the signals transmitted by the transducer, processes the electronic signals received, and presents the resulting images on a display device. Depending on the application and the processing applied to the received signals, the images may represent the spatial variation of the reflected energy itself or other parameters of interest (e.g., the distribution of blood flow velocity, etc.). In medical applications, the image or a sequence of images allow a trained reader to diagnose possible abnormal conditions that otherwise would be unobservable.

BACKGROUND OF THE INVENTION

Many techniques have been developed to transmit and receive ultrasound energy, to process the received data, and to condition the images for display. Typically, the transducer is composed of several individual elements that independently transmit and receive ultrasound energy. To form diagnostically useful images, the received ultrasound energy is focused into beams by summing weighted contributions from the individual elements at carefully selected (and dynamically adjusted) sample times to compensate for the differences in propagation time from each element to points along the beam. Transmit beams are also formed by controlling the relative time of the transmissions from the individual elements. Conventional ultrasound scanners construct image data for a single frame by transmitting and receiving many such beams in succession. The image sequence presented to the human reader and used for diagnosis is constructed from a series of such frames.

The quality of the image sequences produced by conventional ultrasound scanners has several limitations. For example, the frame rate, or temporal resolution, is limited by the propagation time of the ultrasound beams and the fact that constructing a frame of image data requires many sequential beam transmissions. To produce useful image data at acceptable frame rates, ultrasound scanners must process data received from many independent channels (transducer elements) at very high sample rates (e.g., 64 channels at 24 MHz sample rate). This imposes stringent data throughput and computational requirements that are difficult to satisfy. Conventional ultrasound scanners typically address these requirements by incorporating dedicated and highly specialized hardware (e.g., custom designed analog circuitry or digital ASICs) to beamform and to process the resulting data. Because the hardware is so specialized, the functions of these systems are fairly rigidly defined and not easily reconfigurable. Also, once combined by the hardware to form beam data, the original element data are lost (i.e., hardware beamforming is an irreversible process) and are not available for additional processing. For example, if it is desired to form more than one beam from a set of element data by applying different sets of weights and delays (e.g., to increase frame rates), multiple hardware beamformers are required, adding to system complexity, cost, and power consumption.

Another drawback of typical hardware-based beamforming is that it is difficult to use the beamformed data for more than one image modality. The consequence of this is that frame-rates are often dramatically reduced when two or more parametric image sequences (e.g., reflectivity and color velocity) are simultaneously displayed. New parametric image techniques that would expand the diagnostic utility of ultrasound are difficult to achieve because of the rigidity of typical hardware-based beamforming systems.

Spatial resolution is limited by the fact that each transmit beam is typically well focused at only one point (at most) because the relative timing of the respective element transmissions is fixed for each transmission event. Image quality is also limited by the fact that the display coordinates typically do not match the locations where the beams are sampled (e.g., the data may be acquired in polar coordinates, but the image pixels on a display are typically arranged in a rectangular grid). Image formation then requires an interpolation process that is an approximation, resulting in a loss of information.

In addition to the foregoing problems, the information contained in the image data from many conventional scanners is limited to a single two-dimensional plane that has a fixed orientation with respect to the transducer. Methods and apparatuses, typically referred to as 3D/4D systems, have been introduced to address this limitation. These systems interrogate an anatomical volume of interest with ultrasound and reconstruct the received data for the entire volume. A variety of methods may then be used to construct images and image sequences for the entire volume or for desired two-dimensional slices through it. Frame rates and/or spatial resolution are sacrificed, however, because data for the entire volume must be acquired and processed.

BRIEF SUMMARY OF THE INVENTION

The present disclosure is directed to systems and methods which allow for ultrasound parameter estimation to occur at specific advantageous sets of points in a two- or three-dimensional field of view within re-configurable, massively parallel, programmable architectures that can accommodate the input/output streaming, data movement or storage, and computation requirements. In one embodiment, a power efficient system is used for processing the data thereby increasing the ability of the system to be used for hand carried or mobile ultrasound applications.

One aspect of the concepts discussed herein is the architectural aspects which provide the ability to simultaneously accept a large number of channels of data characterized by a continuous, simultaneous flow at high sample rates. The input data is routed at high rates to a distributed and large number of processing elements, memory, and connections for simultaneous parameter estimation at multiple points in the field of view. The ability to route the same data to multiple places enables high frame rates and allows for the streaming of data through the architecture. The ability to reconfigure the system allows for the estimation of various types of parameters at different times or even simultaneously. The architecture is extensible through interconnections between physical devices.

Another aspect to the acquisition of parameter estimation is the use of filters (linear or non-linear) for correcting diffraction and/or propagation effects per channel. These filters also can delay channel data for localizing the estimation of a parameter to a particular locality such as done in beamforming, and controlling signal, clutter, noise, and various forms of resolution. The filtered data may be combined in a number of ways. Acquisition of multiple sets of points for display is possible. For example, multiple planes (lines) through a two- or three-dimensional field of view may be formulated from the same acquired data, thereby avoiding the need for scan conversion and rendering when the sets of points correspond to displayed pixels. It is also possible within this system to localize the parameter estimation process by synthesizing the source signal.

Another aspect to parameter estimation is the ability to re-configure and/or re-program the architecture to apply the proper operations for the estimation of a particular parameter or parameters such as reflectivity, elasticity, strain rate, and motion.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
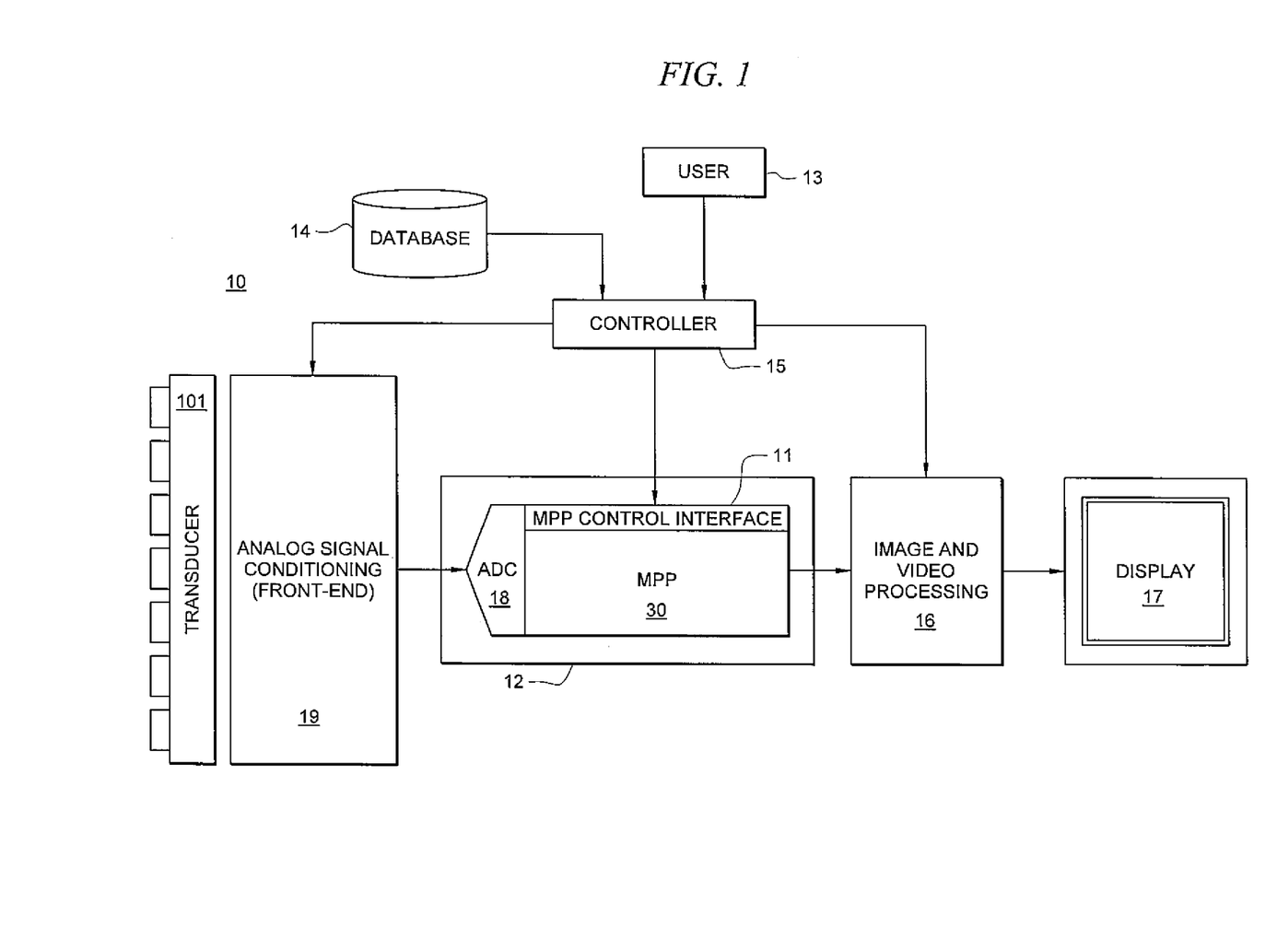
FIG. 1 illustrates one embodiment of a system for employing the techniques of the invention.

FIG. 1 illustrates one embodiment 10 of a system for employing the techniques of the invention. Transducer 101, as is well-known in sonography, sends sound signals into a body, such as a human body, and receives the echoes therefrom. The returned echoes in the form of acoustic information are translated into electrical signals which then, as will be discussed, are used to estimate various parameters at advantageous sets of geometric locations. In one embodiment, this estimation is accomplished by Massively Parallel Processors (MPP) 30 for presentation to user 13. Front end 19 receives the return electrical signals from the ensonified volume, compensates and filters this data and then presents this volume data to analog to digital converter (ADC) 18. These digitized signals representing the return echoes (energy response) may be streamed through MPP subsystem 12.

One embodiment of MPP subsystem 12 is depicted in three parts. MPP 30 performs beam forming, signal processing, parameter estimation, and other operations to create images suitable for the user using signals from ADC 18. MPP control interface 11 configures MPP 30 to perform the appropriate functions based on instructions that are received from controller 15 which, in turn, are based upon selections from the user 13.

Database 14 supplies pre-determined and default processing control variables required by MPP 30. Data from MPP 30 is passed along to image and video processing 16 for further formatting and processing of data for presenting to the user through Display 17. In one embodiment, elements 12, 14, 15, 16, and 17 can be contained in a device weighing 10 lbs. or less.

Figure 2:
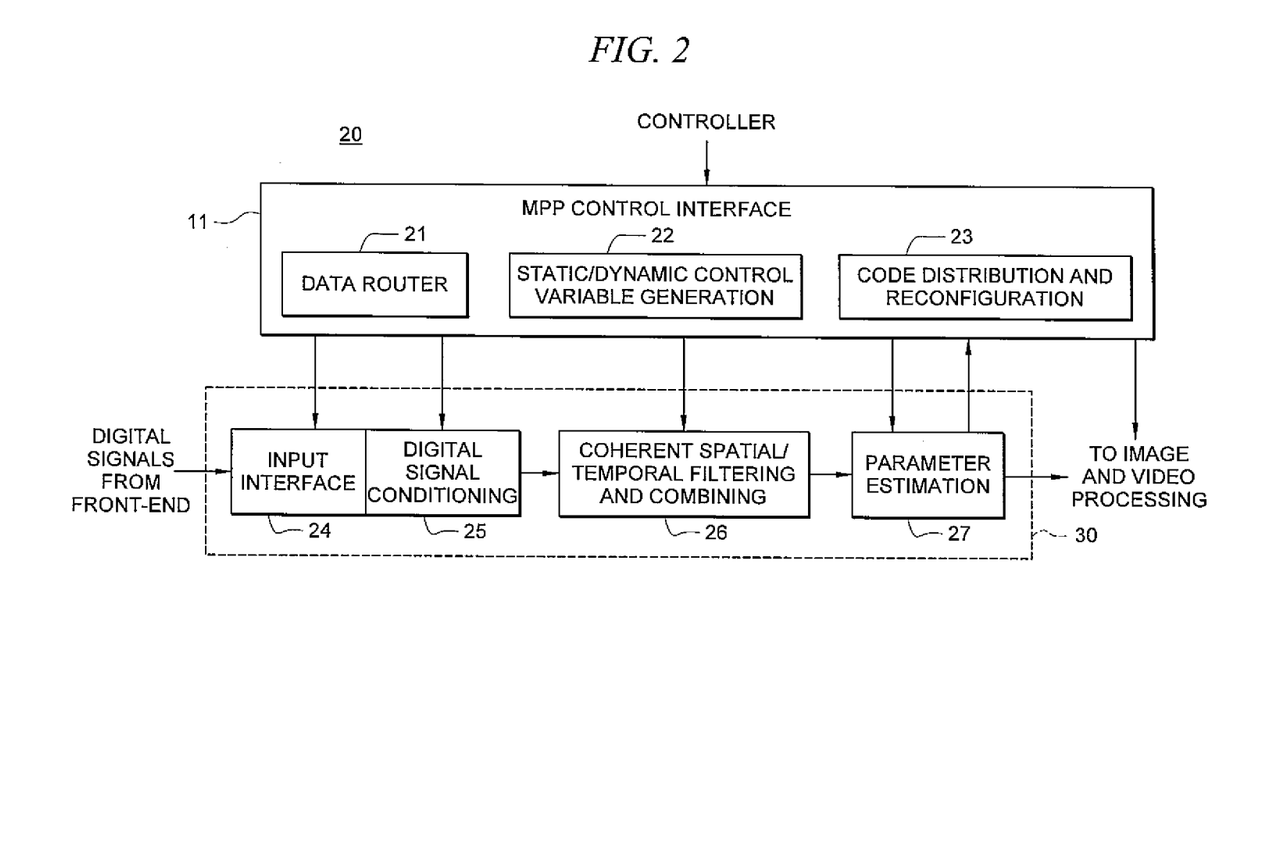
FIG. 2 illustrates one embodiment of some of the architectural elements within the invention.

FIG. 2 illustrates one embodiment 20 of some of the elements within MPP Subsystem 12. Digital signals from ADC 18 are received by input interface 24 and formatted to be presented to digital signal conditioning process 25 which performs signal processing operations, typically filtering, that are advantageous to apply prior to beam formation.

The conditioned data is then presented to coherent spatial/temporal filtering and combining process 26. This function seeks to enhance and localize, typically with some form of filtering, whether it be linear or non-linear, the accurate estimation of parameters at advantageous sets of geometrical locations Some functions performed here, that are well known by those experienced in the art, are demodulation, beam forming including multi-line beam forming, cross correlation, normalization, multi-rate quadrature band pass (QBP) filtering, Doppler wall filtering, and fast Fourier transforms (FFT) which among other advantages improve signal to noise and clutter. These functions may be also used to improve various forms of resolution metrics, including axial resolution, lateral resolution, contrast resolution, and detail resolution. The generation of parameters to support these functions is also a function suitable to process 26.

Image data that are localized and enhanced at geometrically advantageous geometric locations are then presented to parameter estimation process 27 which generates the particular estimates of the type of parameters to be used for display. Some functions performed here, that are well known by those experienced in the art, are detection of signal intensity, compression, Doppler wall filter filtering for flow imaging, segmentation, velocity estimation, strain estimation, strain rate estimation, classification, spatial compounding, scan conversion, rendering, and spatial-temporal image processing.

One embodiment of MPP control interface 11 performs three functions. As will be described hereinafter, data router 21 configures the connectivity of the distributed bus architecture of MPP 30 to effectively route data among the distributed processing elements and memory devices. Static and dynamic control variable generator 22 distributes and/or creates control variables required for the various data processing functions. Some of these control variables may be pre-computed and retrieved from database 14 (FIG. 1) while others may be newly generated using, for example, processors within MPP 30. Finally, code distribution and reconfiguration process 23 governs what processing algorithms are to be accomplished on which processors and in which order.

Figure 3:
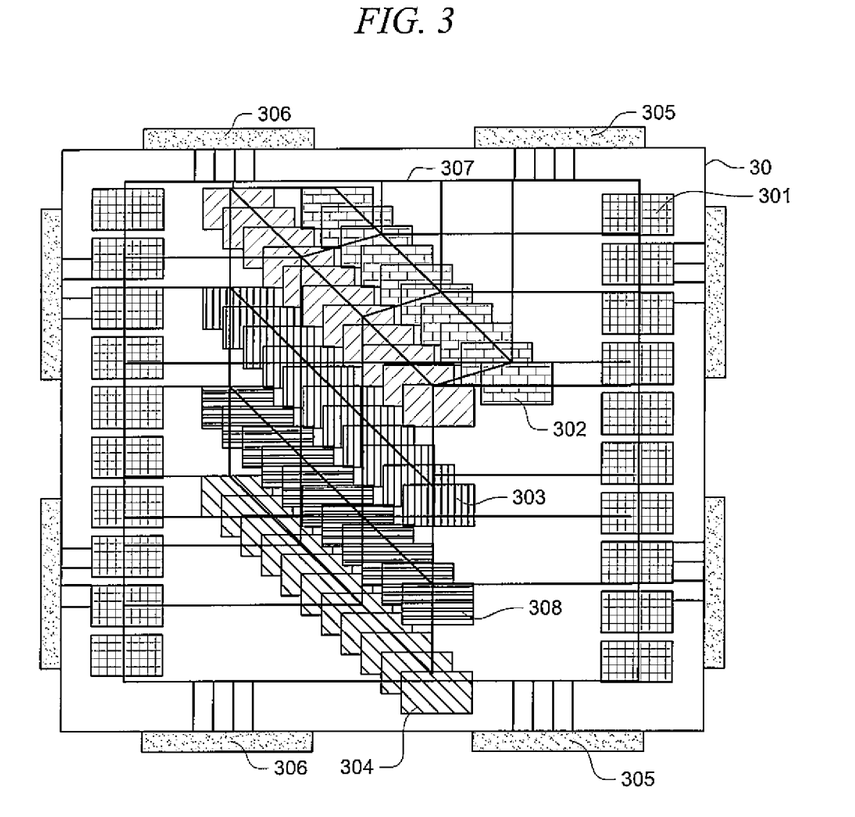
FIG. 3 illustrates one embodiment of a physical device conforming to the architectural elements within the invention.

FIG. 3 shows one embodiment of massively parallel processor (MPP) 30. The actual form which the hardware (ASIC, FPGA, etc.) takes is not critical to the operation of the concepts discussed herein. These concepts rely, instead, on a massively parallel, re-configurable, and distributed network of processing elements, memory, and communication or equivalent thereto. These features enable the high aggregate rates of data movement required by ultrasound and reduce high bandwidth demands on memory devices by enabling streaming of data, multiple and simultaneous use of data, and re-routing of data. Moreover, these features enable the functionality to be changed or multiple functions corresponding to different ultrasound modalities to be configured for simultaneous operation even using the same echo returns.

The internal processors are interconnected by a distributed network of connections which allow for efficient transfer and replication of data. Ultrasound applications have high bus bandwidth requirements which are more easily satisfied with a distributed network of buses. Port 306 allows this particular processor to extend communicating to other processors on other MPP devices. Ports 305 are similar types of ports which allow wide bandwidth data input and output to the MPP. Fabric 307 allows connectivity to occur among and between individual processors such that, if necessary, data produced by one processor can be used simultaneously by several other processors. This then allows for efficient replication of data. Moreover, this allows beam forming to be simultaneously processed at multiple sets of geometrical locations.

It is envisioned that the individual processors making up the MPP will carry out their designated operations independently of each other except for the flow of data. They will also be able to be configured or rapidly re-configured to perform individual operations which when appropriately connected performs useful ultrasound applications. These processors need not be homogeneous. In the embodiment shown, there are several different types of processors, 301, 302, 303, 304, etc. Some types of processors are optimized for specific functions while others handle more general purpose processing needs. The optimized processors may be functional acceleration units (specialized processors) to carry out dedicated functions with greater efficiency than the general purpose processors for ultrasound applications. For example, one type of processor may be particularly suited for geometric transformations while another may be suited for accelerating fast Fourier transforms or cross correlations.

It is envisioned that the memory is also distributed in order to accommodate the high memory bandwidth needs of ultrasound applications. To accomplish this, data is stored, for example on distributed memories 308, in association to where that data is required to be used and not according to a centralized memory architecture typical of the microprocessor architectures of personal computers.

In operation, MPP 30 can receive a multiplexed, encoded set of individual channels or individual elements from the array via ports 305. This data is then processed, on a channel by channel basis, in a manner required for that channel at that moment in time. The processing depends, at least in part, on the user selected surfaces through the ensonified volume. Since the different or same channels can be processed differently and repeatedly, the system allows for the desired processing at the desired surfaces defined by the advantageous sets of geometrical locations. The use of streaming in such architecture reduces power requirements as it avoids massive usage of memory.

Returning now to FIG. 1, MPP control interface 11 provides information to MPP 30 for controlling the individual MPP devices, thereby allowing for the selection of one or more different surfaces to be presented concurrently. The configuration of the MPP devices can be static, which means that control variables and configuration information are pre-computed and retrieved by the controller from the database. The configuration can be dynamic in that selections for the configurations by the user, or other source, are given to the MPP subsystem which computes new processing control variables and configuration settings.

Figure 4:
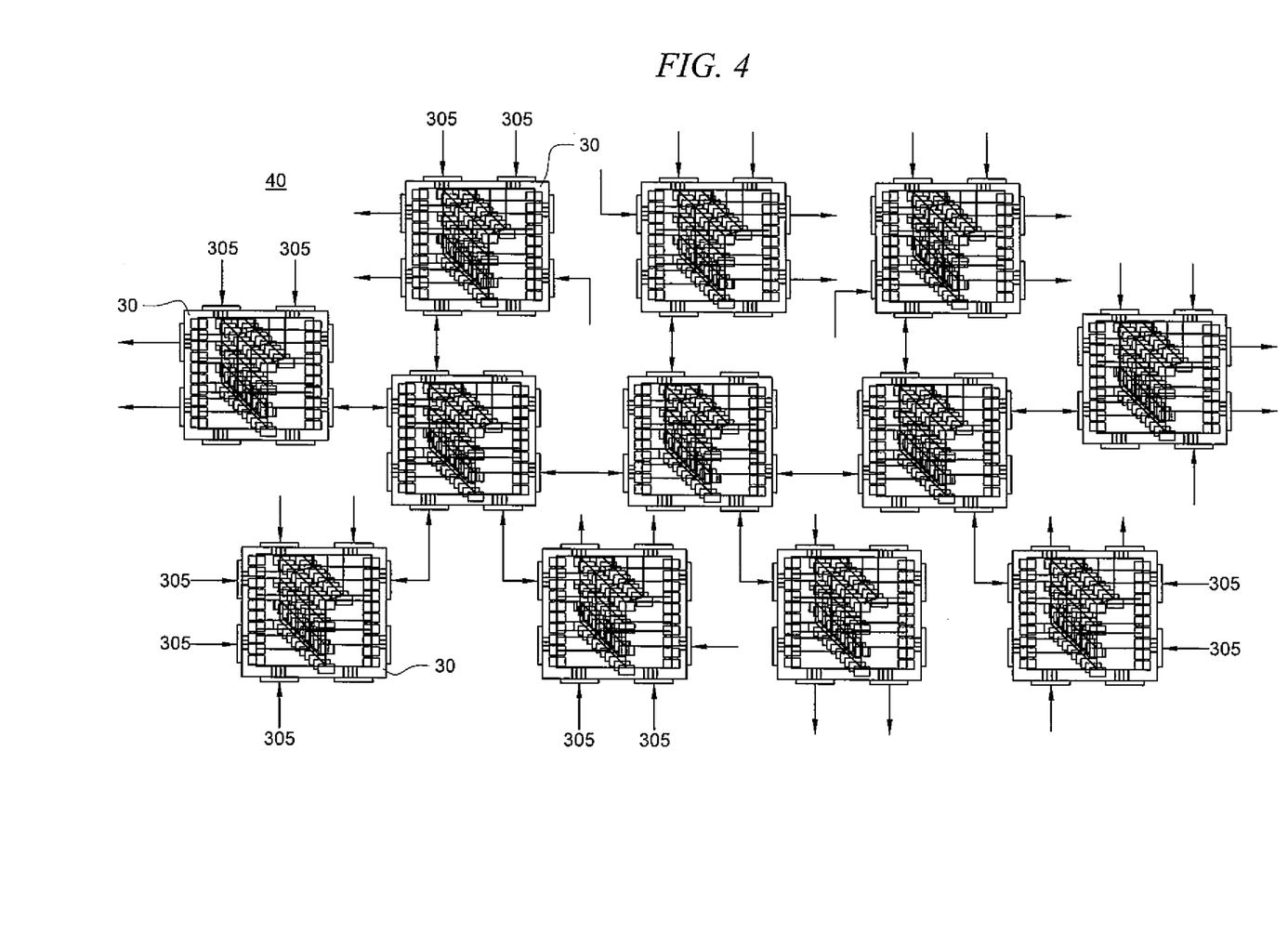
FIG. 4 illustrates one embodiment of interconnected processors which extend the architectural elements of the invention.

FIG. 4 shows one embodiment 40 of the interconnection of MPPs 30. Ports 305 and 306 are used for collecting data from the transducer as well as for connecting with other similar MPP devices. This allows for the efficient transfer of data and for the overall compute power to be increased as needed to accommodate the required signal or image processing. This also allows for assigning more or less individual processing elements, such as arithmetic logic units, memory, storage, etc. into a data stream for processing. The control of the processors, as well as the functions performed by the different processors, can be controlled, as discussed, by programmable digital processing elements. This programming can be accomplished by a variety of techniques, including, for example, machine language code or binary images. The elements could contain, if desired, field programmable gate arrays (FPGA).

Figure 5:
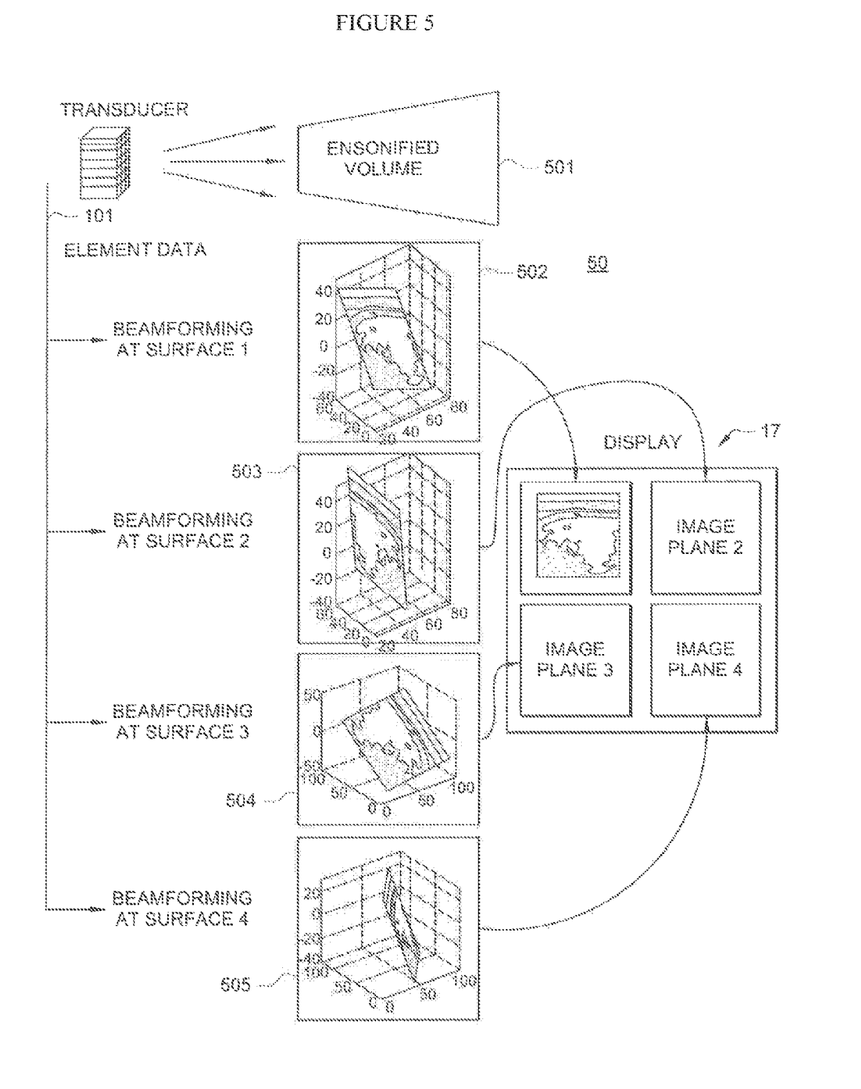
FIG. 5 illustrates one embodiment of a system for employing the parameter acquisition techniques of the invention.

FIG. 5 shows one embodiment 50 of the non-traditional ultrasound imaging capability that is afforded by the concepts discussed herein. In this embodiment, transducer 101 (FIG. 1) is used to ensonify a volume 501. Volume 501 is depicted as a two-dimensional array although analogous imaging can be performed by other transducer element arrangements to form, if desired, a three-dimensional array or one-dimensional array. As conditioned, digitized, return echoes are able to be replicated by the architecture, simultaneous beam forming can be accomplished along multiple surfaces 502, 503, 504, and 505 using the same ensonified volume data 501. This is of significant advantage to ultrasound imaging as only one ensonification sequence is required to form multiple images as with the case of 3D/4D modality where multiple and orthogonal planes are typically presented. This allows greatly improved frame rates to be displayed, for example, on display 17.

Although the surfaces in FIG. 5 indicate planes, other surfaces can be more advantageous. Such surfaces might also include contours along anatomical features, such as along boundaries of the heart or other organs. Also, the system could be made to beam form to pre-determined surfaces rotated or translated in several degrees of freedom by the user. At any point in time the user can select separate surfaces and present the selected surfaces concurrently on different portions of the display screen. Some of the views could be from planes that are rotating or otherwise changing so as to present a changing image on the display. Thick surface or stacked parallel surfaces may also be acquired for rendering purposes. All of these views of the target image are anchored without necessarily moving transducer 101. In one embodiment, the MPP system is used to assist in computing new control variables to quickly reconfigure the system for the user directed imaging selections. Flexibility is required since the system must be able to quickly reconfigure the computation based on the user input.

It is easily seen that the time course of imaging parameters along an arbitrary contour through the field of view can be accurately and efficiently measured and displayed.

Another advantage to the acquisition approach of this invention implicit in FIG. 5, is the ability to form beams at geometrical locations that directly correspond to pixels on the display. In this way, approximations and unwanted artifacts of scan conversion, rendering, and beam under-sampling can be avoided which greatly improves image quality. Zooming an image may be implemented by this invention as forming beams to a new, more dense set of geometrical locations corresponding to the desired locations of the new pixel centers.

Furthermore, since beam formation occurs at pixel locations, the number of different planes to be displayed simultaneously on the display does not increase beamforming requirements and frame rates need only be limited by the deepest depth in the field of view.

Note that in addition to displaying images that represent the intensity of the sound reflected along a selected plane, other parametric images can be formed to present different tissue properties, such as strain or other modalities that require additional processing. These different modalities may be performed simultaneously with the same received echoes, which greatly improves imaging rate. Also, it is desirable to provide multiple images of surfaces or volumes without moving the transducer. For example, as discussed, the imaging display is partitioned so as to present different images of the same target simultaneously without moving the transducer. Each window of the display may show a different projection of the volume acquisition signal or different parameters thereof. Also, size can be varied with respect to each window.

Figure 6:
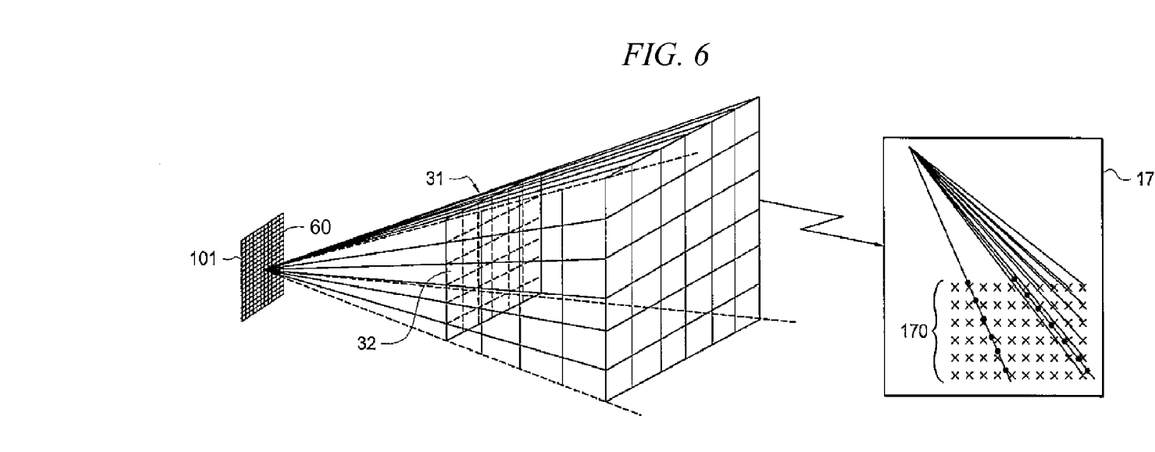
FIG. 6 illustrates one embodiment of a voxel volume in which desired grids can be formed for subsequent image presentation.

FIG. 6 illustrates one embodiment of a voxel volume in which desired grids can be fanned for subsequent image presentation. Transducer 101, as discussed above, provides the acoustic emissions on several channels. For ease of discussion, all of these emissions are shown to come from a single point 60. The time delays established by the filters (as discussed above) are such as to allow for geometric expansion shown in FIG. 6 as if the data did actually come from a single point. Thus, at the center of the array the delay can be thought of as zero. On the ends of the array it takes more time for the sound to arrive so the added delay at the center is greater than at the edges. This aligns the data as if it all came from a single point in space. The rays are the centers of the beam. One or more planes, such as plane 32, can be formed within voxel space 31 at any point or at any desired angle. The desired plane (plane 31 in this example) has within it a grid of data points representing the channels from transducer 101. Each of these data points are mapped directly to a pixel within pixels 170 of the display 17. This then allows for a mapping between a point in space and a particular pixel on a display screen.

Figure 7A:
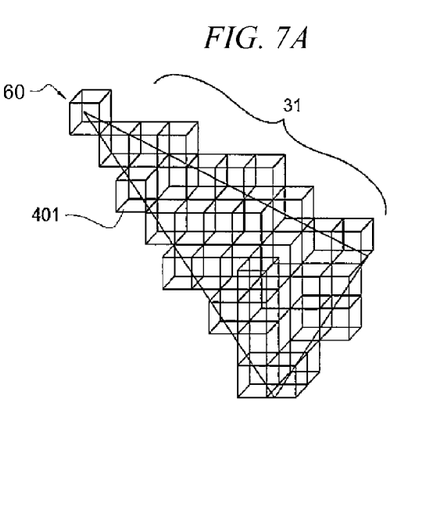
FIGS. 7A through 7E show embodiments of grids taken through the voxel volume of FIG. 6.
Figure 7B:
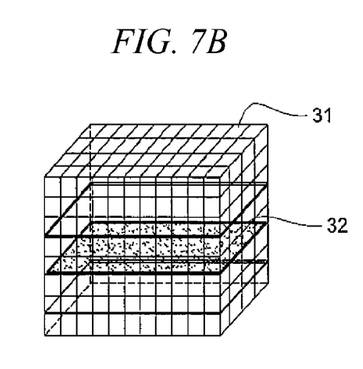
Figure 7C:
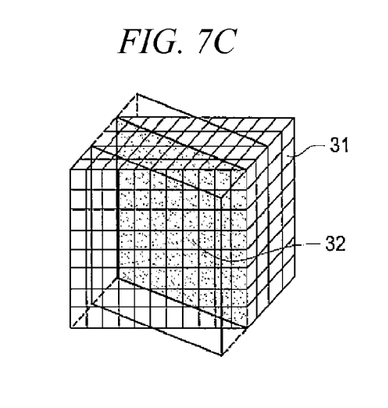
Figure 7D:
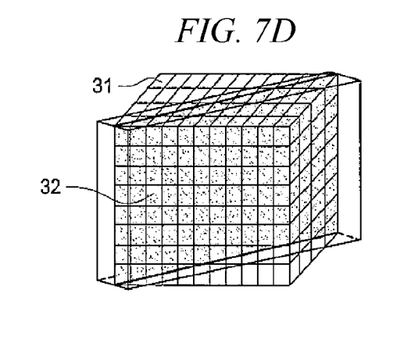
Figure 7E:
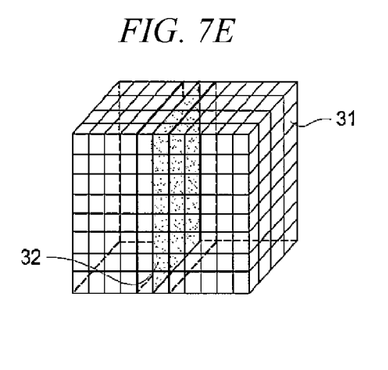

FIG. 7A shows a progression of grids, such as grid 401, radiating outward from point 60. Grids 401 are within voxel space 31. Within voxel space 31 any of a number of planes 32 can be established with each plane having a particular set of data points (as determined by the intersection of the desired plane and the channels within voxel space 31. Since each plane intersects the voxel space channels at a different place (depending upon angle, distance, circumference, etc.), the data at each such intersection (thought of as a grid) is different. Since each intersection of the plane with the grid is mapped directly to a particular pixel, the image formed on the screen from each grid is dependent upon the selection of the plane relative to voxel space 31.

FIGS. 7A through 7E show four such planes intersecting the voxel space at different angles. Note that the intersection need not necessarily be flat in Cartesian coordinates, but can be at constant range coordinates from the center of the transducer or at any other desired geometry. Also note that the plane need not be held flat but could rotate in multiple degrees of freedom through the voxel space volume.

At any point in time the user can select separate planes and present the selected planes concurrently on different portions of the screen. Some of the views could be from planes (grids) that are rotating or otherwise changing so as to present a changing image on the display. All of these views of the target image are anchored without moving transducer 101.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for creating sonographic images, the method comprising:

processing transduced data from a single ensonification sequence using one or more massively parallel processors formed from a plurality of processors in communication with each other, the processing including— replicating echo signals from a portion of the data from the single ensonification sequence to form multiple simultaneous display images by simultaneous beam forming along multiple surfaces, wherein the beam forming occurs a individual points on each surface that are mapped directly to corresponding pixels on a display, and wherein the data for each pixel is beam formed at a single point on the surface; and providing pre-determined and default processing information to the one or more individual massively parallel processors from a control interface to allow one or more different surfaces to be presented concurrently.

2. The method of claim 1 wherein said processing is accomplished without reducing a frame rate of any image.

3. The method of claim 1 wherein each of said multiple simultaneous displayable images is representative of an energy response at a target area of each of the multiple surfaces and wherein said simultaneous displayed images are produced without requiring physical movement of a transducer with respect to said target area.

4. The method of claim 1 wherein said processing is accomplished using a distributed parallel processing network of digital processing elements.

5. The method of claim 4 wherein said method is practiced in a device weighing ten pounds or less.

6. The method of claim 4 further comprising:

reconfiguring said digital processing elements dependent upon desired displayable parameters of one of said multiple simultaneous displayable images.

7. The method of claim 6 wherein said processing network comprises at least 32 processing elements.

8. The method of claim 1 wherein said processors include general purpose processors and specialized processors.

9. The method of claim 1 wherein at least one of the surfaces is curved.

10. A method of creating sonographic images with an ultrasound device comprising:
creating image data of a target area by simultaneous beam forming at multiple surfaces through the target area using transduced data received from the target area in a single ensonification sequence, wherein at least one of the multiple surfaces is beam formed at individual points that are mapped directly to corresponding pixels on a display, and wherein the data for each pixel is beam formed at a single point on the at least one of the multiple surfaces; and
providing pre-determined and default processing information to one or more massively parallel processors from a control interface to allow image data of one or more different surfaces to be presented concurrently.

11. The method of claim 10 further comprising:
displaying selected points of the set of points on the display.

12. The method of claim 10 wherein the ultrasound device weighs ten pounds or less.

13. The method of claim 10 wherein the image data is representative of an energy response at the target area and wherein the image data can be produced without requiring physical movement of a transducer with respect to said target area.

14. The method of claim 10 further comprising:
reconfiguring the one or more massively parallel processors dependent upon desired displayable sets of points.

15. The method of claim 10 wherein at least one of the massively parallel processors includes a processing network comprising at least 32 processing elements.

16. The method of claim 15 wherein a function of the processing elements can be reconfigured.

17. The method of claim 15 wherein the at least 32 processing elements are capable of operating independent of each other.

18. The method of claim 10 wherein the creating and defining are accomplished by arithmetic logic units (ALUs) each operating on a single stream of data.

19. The method of claim 18 wherein said ALUs are individually programmable.

20. The method of claim 10 further comprising:
concurrently displaying additional images of said target area as defined by image data at other defined sets of points taken with respect to said created image data.

21. The method of claim 20 wherein each of said sets of points are on surfaces different from each other.

22. The method of claim 21 further comprising:
processing said image data within each said set of points independently from each other.

23. The method of claim 22 wherein said independent processing is at least one processing function selected from the list of:
filtering, weighting, delaying, summing, combining, rendering, volume rendering, non-linear processing, spatial or temporal filtering; 2D processing, velocity measurement, tissue characterization, 3D processing, reflectivity, strain rate, speed of sound, density, scattering, elastic parameters.

24. The method of claim 22 wherein said independent processing comprises using different processors for data points within each defined set of points.

25. The method of claim 24 wherein some of said processors are special purpose processors.

26. The method of claim 24 wherein data processed by one of the processors is stored in distributed locations.

27. A system for ultrasound imaging, the system comprising:
means for ensonifying a volume of interest at a target area;
means for receiving an acoustic response from the volume of interest;
means for digitizing received acoustic responses; and
a massively parallel distributed, reconfigurable network of digital processing elements, wherein the network comprises:
a plurality of distributed digital processing elements;
a plurality of distributed memory elements; and
a distributed bus architecture connecting the plurality of processing elements within the plurality of memory elements, thereby enabling communication interconnections operable for selectively creating in real-time at least one displayable image from the digitized received acoustic response, wherein the at least one displayable image is created by beam forming beam echo signals received from one of multiple surfaces, wherein the beam forming occurs at individual image points that are mapped directly to corresponding pixels on a display, and wherein the data for each pixel is beam formed at a single point on the surface.

28. The system of claim 27 having at least 32 said digital processing elements.

29. The system of claim 28 wherein said programmable digital processing elements are integrated circuits.

30. The system of claim 28 wherein said displayable images are based upon selected acoustic parameters.

31. The system of claim 28 wherein said images are selected from different modalities.

32. The system of claim 28 wherein said ensonifying means comprises:
at least one transducer having a plurality of elements and wherein said ensonified volume is formed by combining data from more than one of said elements.

33. The system of claim 32 wherein a plurality of the different displayable images are created from echo signals received from a common ensonified volume.

34. The system of claim 33 wherein at least some of the data received from the ensonified volume is reused to form said plurality of images.

35. The system of claim 28 wherein said massively parallel processing elements comprise:
programmable digital processing elements and wherein said digitized acoustic response is streamed through said programmable elements.

36. The system of claim 28 wherein some of said processors are general purpose processors and some of said processors are specialized processors.

37. The system of claim 28 wherein said network is reconfigurable by software.

38. The system of claim 28 further comprising at least one filter for compensating for propagation time differences between said elements.

39. The system of claim 38 wherein at least one of said filters is adapted to perform at least some spatial filtering, temporal filtering, or a combination of spatial and temporal filtering.

40. The system of claim 27 wherein said points represent locations on a surface within said ensonified volume.

41. The system of claim 28 wherein the system further comprises:
processing elements arranged to reconfigure the beam forming of the beam echo signals based on detected image features.

42. The system of claim 27 wherein said reconfiguring does not require motion of said ensonifying means.

43. The system of claim 27 further comprising means for selectively routing data through said network in response to user input.

44. The system of claim 28 weighing ten pounds or less.

45. A system for processing data from a sonographic transducer, the system comprising:
a plurality of parallel distributed programmable digital processors;
an interconnection fabric for allowing the processors to process a spatial volume of one or more sets of image data, the one or more sets of image data created from data generated by a sonographic transducer in a single ensonification sequence; and
control circuitry, including the fabric, for allowing a user to define at least one surface within the spatial volume, the surface generated by beam forming echo signals received from the spatial volume, wherein the control circuitry is configured to beam form the one or more sets of image data at individual points that are mapped directly to corresponding pixels on a display, and wherein the data for each pixel is beam formed at a single point of the more sets of image data.

46. The system of claim 45 wherein said fabric comprises:
data routing switches;
data routing paths;
control elements; and
distributed memory.

47. The system of claim 46 further comprising;
a display; and
means for presenting on said display at least one image of said target area as defined by image data corresponding to coordinates on said defined surfaces.

48. The system of claim 45 wherein the display is configured to present concurrently a plurality of images of said target area of other defined surfaces of said spatial volume.

49. The system of claim 48 wherein said independent processing allows for processing functions selected from the list of:
filtering, weighting, delaying, summing, combining, rendering, volume rendering, non-linear processing, spatial or temporal filtering; 2D processing, velocity measurement, tissue characterization, 3D processing, reflectivity, strain, rate, speed of sound, density, scattering, elastic parameters.

50. The system of claim 48 wherein images from different surfaces are not necessarily processed using the same processing functions.

51. The system of claim 45 wherein all of said processors do not necessarily perform the same functions.

52. A sonographic method comprising:
delivering a pattern of sound waves into a body and for receiving back from the body energy responses of tissues impacted by the sound waves, the received energy responses forming an ensonified volume; and
estimating parameters from a subset of the received energy responses within the ensonified volume proximate to a selected surface of interest to create an image, the parameters including reflectivity, elasticity, strain rate, and motion of the selected surface of interest, wherein the image is created by beam forming at the selected surface of interest; and
displaying the image on a display that has a plurality of pixels with corresponding pixel values, wherein the pixel value of each pixel is determined by data beam formed at a single corresponding point at the selected surface of interest.

53. The method of claim 52 further comprising:
establishing multiple surfaces within said volume; and
concurrently presenting on the display different images of said parameters.

54. The method of claim 52 wherein the surface establishing comprises processing energy responses within the volume using a network of massively parallel processing elements, the method further comprising:
using a plurality of distributed digital processing elements, a plurality of distributed memory elements, and a distributed bus architecture connecting the plurality of processing elements with the plurality of memory elements for selectively estimating the parameters.

* * * * *